(12) United States Patent
Vacher et al.

(10) Patent No.: US 9,433,603 B2
(45) Date of Patent: Sep. 6, 2016

(54) USE OF 3-(R)-[3-(2-METHOXYPHENYLTHIO)-2-(S)-METHYLPROPYL]AMINO-3,4-DIHYDRO-2H-1,5-BENZOXATHIEPINE FOR PREVENTING AND/OR TREATING CARDIOTOXIC EFFECTS CAUSED BY CHEMOTHERAPY AND/OR RADIATION

(75) Inventors: Bernard Vacher, Castres (FR); Bruno Le Grand, Teyssode (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/344,154

(22) PCT Filed: Sep. 13, 2012

(86) PCT No.: PCT/EP2012/067980
§ 371 (c)(1),
(2), (4) Date: Mar. 11, 2014

(87) PCT Pub. No.: WO2013/037905
PCT Pub. Date: Mar. 21, 2013

(65) Prior Publication Data
US 2014/0235692 A1    Aug. 21, 2014

(30) Foreign Application Priority Data

Sep. 13, 2011 (FR) ...................... 11 58155

(51) Int. Cl.
A61K 31/39 (2006.01)

(52) U.S. Cl.
CPC ...................... *A61K 31/39* (2013.01)

(58) Field of Classification Search
CPC ................................... A61K 31/39
USPC ....................................... 549/10
See application file for complete search history.

(56) References Cited

U.S. PATENT DOCUMENTS

| 7,109,234 B2 * | 9/2006 | Vacher et al. ................. 514/431 |
| 7,132,547 B2 * | 11/2006 | Ishihara et al. ............ 548/306.4 |
| 2004/0127552 A1 | 7/2004 | Vacher et al. |

FOREIGN PATENT DOCUMENTS

| FR | 2822467 A1 | 9/2002 |
| WO | WO 02/081464 A1 | 10/2002 |
| WO | WO 2011/003129 A1 | 1/2011 |

OTHER PUBLICATIONS

Zisterer et al, Pyrrolo-1,5-benzoxazepines Induce Apoptosis in HL-60, Jurkat, and Hut-78 Cells: A New Class of Apoptotic Agents, The Journal of Pharmacology and Experimental Therapeutics vol. 293, No. 1 pp. 48-59 (2000).*
Belardinelli et al., "Inhibition of the late sodium current as a potential cardioprotective principle: effects of the late sodium current inhibitor ranolazine," Heart, 2006, pp. iv6-iv14, XP-002672468.
Eschenhagen et al., "Cardiovascular side effects of cancer therapies: a position statement from the Heart Failure Association of the European Society of Cardiology," Nature Reviews, European Journal of Heart Failure, vol. 13, 2011, pp. 1-10.
Ewer et al., "Cardiotoxicity of anticancer treatments: what the cardiologist needs to know," Nature Reviews, Cardiology, vol. 7, Oct. 2010 (Published online Aug. 24, 2010), pp. 564-575, XP009157868.
Gillet et al., "Beneficial effects of omega-3 long-chain fatty acids in breast cancer and cardiovascular diseases: voltage-gated sodium channels as a common feature?" Biochimie, vol. 93, 2011 (Available online Feb. 16, 2010), pp. 4-6.
Hong et al., "Cardio-Oncology/Onco-Cardiology," Clinical Cardiology, vol. 33, No. 12, 2010, pp. 733-737.
Létienne et al., "Myocardial protection by F 15845, a persistent sodium current blocker, in an ischemia-reperfusion model in the pig," European Journal of Pharmacology, vol. 624, 2009 (Available online Sep. 22, 2009), pp. 16-22.
Li et al., "Preventive Effect of Erythropoietin on Cardiac Dysfunction in Doxorubicin-Induced Cardiomyopathy," Circulation, Journal of the American Heart Association, vol. 113, Jan. 31, 2006, pp. 535-543.
Li et al., "Thrombopoietin Protects Against In Vitro and In Vivo Cardiotoxicity Induced by Doxorubicin," Circulation, Journal of the American Heart Association, vol. 113, May 9, 2006, pp. 2211-2220.
Saint, "Persistent (current) in the face of adversity . . . A new class of cardiac anti-ischaemic compounds on the horizon?" British Journal of Pharmacology, vol. 156, 2009 (published online Jan. 7, 2009), pp. 211-213, XP-002672467.
Senkus et al., "Cardiovascular effects of systemic cancer treatment," Cancer Treatment Reviews, vol. 37, 2011, pp. 300-311.
Singal et al., "Doxorubicin-Induced Cardiomyopathy," The New England Journal of Medicine, vol. 339, No. 13, Sep. 24, 1998, pp. 900-905, XP-002672469.

* cited by examiner

*Primary Examiner* — Taofiq A Solola
(74) *Attorney, Agent, or Firm* — Birch, Stewart, Kolasch & Birch, LLP

(57) ABSTRACT

The present invention relates to the use of 3-(R)-[3-(2-methoxyphenylthio)-2-(S)-methylpropyl]amino-3,4-dihydro-2H-1,5-benzoxathiepine or a pharmaceutically acceptable salt thereof for preventing and/or treating cardiotoxic effects caused by chemotherapy and/or radiation.

22 Claims, 1 Drawing Sheet

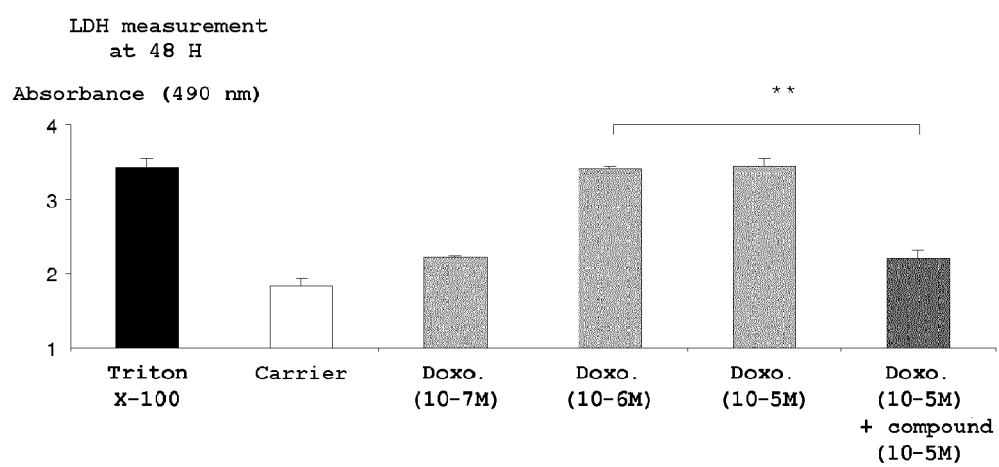

USE OF 3-(R)-[3-(2-METHOXYPHENYLTHIO)-2-(S)-METHYLPROPYL]AMINO-3,4-DIHYDRO-2H-1,5-BENZOXATHIEPINE FOR PREVENTING AND/OR TREATING CARDIOTOXIC EFFECTS CAUSED BY CHEMOTHERAPY AND/OR RADIATION

The invention concerns 3-(R)-[3-(2-methoxy phenylthio)-2-(S)-methyl-propyl]amino-3,4-dihydro-2H-1,5-benzoxathiepine or one of its pharmaceutically acceptable salts for use in the prevention and/or treatment of cardiotoxic effects due to chemotherapy and/or anticancer radiation.

3-(R)-[3-(2-methoxyphenylthio)-2-(S)-methyl-propyl]amino-3,4-dihydro-2H-1,5-benzoxathiepine represented by the formula:

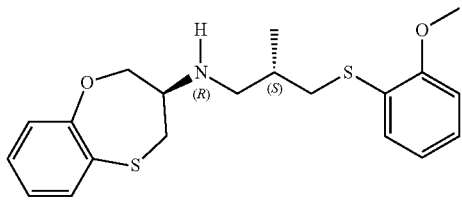

its pharmaceutically acceptable salts and use thereof in the treatment of angina pectoris, heart failure, myocardial infarction, cardiac rhythm disorders are described in patent WO 02/081464.

Cancer can be very broadly defined as a disease related to the proliferation and uncontrolled dissemination of cells of the body which have become abnormal. It is one of the leading causes of mortality in developed countries and the number of new cases is constantly increasing. However, through progress in anticancer treatments inter alia, the death rate from cancer has been significantly reduced. Anticancer treatments, depending on the type and stage of progress of the disease, include surgery, radiotherapy and chemotherapy. In most cases a combination of two or three approaches is necessary.

Radiotherapy is a loco-regional method for treating cancer, using ionising radiation to destroy the cancer cells whilst preserving healthy neighbouring tissue inasmuch as is possible. By the term << ionising radiation >> is meant charged or non-charged particles or energy rays capable of transmitting their energy to the irradiated cell. Ionising radiation deteriorates the structure of the macromolecules and perturbs the main functions of cellular life.

Chemotherapy concerns the use of synthetic or natural substances able to kill or limit the proliferation of cancer cells. By << conventional chemotherapy >> is meant chemotherapy based on the use of cytotoxic agents. By << targeted chemotherapy >> is meant the use of active agents on a precise biological target involved in the process of cancerogenesis.

Anticancer chemotherapy whether targeted or conventional interferes with mechanisms present in most types of cells and involved in the growth, survival and/or multiplication of cells. On this account it compromises cell homeostasis not only in the cancer tissues but also in non-cancerous tissues of the body. The corollary of this lack of selectivity for cancer cells is a major toxicity.

The heart is particularly sensitive to the systemic action of chemotherapy substances and ionising radiation. Since heart tissue is not or only scarcely renewed, the heart muscle cells (cardiomyocytes) are naturally protected against apoptosis. Yet, the mechanisms used by the main anticancer drugs and by ionising radiation are precisely based on the reactivation/stimulation of pro-apoptotic routes and/or the inhibition of anti-apoptotic routes.

For example, in cured patients or patients with lengthy remission it is found that mortality from cardiovascular diseases due to anticancer treatments exceeds that associated with a recurrence or the onset of a new cancer.

Anticancer drugs can be schematically classified into several categories according to their cellular targets and/or mechanism of action:
cytotoxic agents:
 alkylating agents and similar: they have functions capable of binding to numerous nucleophilic substrates. These reactive groups particularly attach themselves onto DNA and form bridges within or between the strands thereby blocking its replication. As examples of alkylating agents mention can be made of alteramine, busulfan, carboplatin, carmustine, chlorambucil, chlormethine, cisplatin, cyclophosphamide, dacarbazine, estramustine, fotemustine, ifosfamide, lomustine, mechlorethamine, melphalan, mitomycin C, oxaliplatin, pipobroman, procarbazine, streptozocin, temozolomide, thiotepa trabectedin, trophosphamide, uramustine.
 antimetabolites: these are structural analogues of natural metabolites, they interfere with the synthesis of nucleic acids and are therefore chiefly active during the S phases of the cell cycle. These drugs act by inhibiting the enzymatic pathways involved in the de novo synthesis of purine or pyrimidine bases, or by incorporating themselves in their stead in DNA. As examples of antimetabolites mention can be made of azathioprine, capecitabine, cladribine, cytarabine, cytosine arabinoside, floxuridine, fludarabine, 5-fluoro-uracil, gemcitabine, 6-mercaptopurine, methotrexate, pemetrexed, pentostatin, raltitrexed, tegafur, thioguanine.
 DNA modifiers: this class includes inhibitors of topoisomerases which are enzymes causing temporary DNA cleavage. Topoisomerases I and II respectively cause double-strand and single-strand breaks. The inhibitors of topoisomerases bind to the topoisomerase-DNA complex at the cleavage stage and prevent the re-ligating step. The inhibitors of topoisomerase I comprise irinotecan and topotecan. As inhibitor of topoisomerases II mention can be made of etoposide, mitopodoside, teniposide. Among the DNA modifiers there are also intercalating agents such as the anthracyclines e.g. aclarubicin, daunorubicin, doxorubicin, epirubicin, idarubicin, pirarubicin, zorubicin, and the anthracenediones such as mitoxantrone for example. These molecules have a planar structure enabling them to intercalate within the DNA double helix which causes its deformation and blocks transcription and replication. These derivatives additionally have action on the topoisomerases which they inhibit.
 Anthracyclines also belong to the family of antitumour antibiotics, which itself groups together compounds such as bleomycin, dactinomycin or actinomycin D for example.
 Mitotic spindle poison derivatives: two groups of molecules are represented in this class. The first group concerns the vinca-alkaloids such as vinblastine, vincaleukoblastine, vincristine, vindesine, vinflunine, vinorelbine and more recently eribulin, a synthetic analogue of a natural product, halichondrin B, extracted from sponges. The second group comprises the taxanes e.g. docetaxel, paclitaxel, and the epothilones such as ixabepilone approved for the treatment of breast cancers resistant to taxanes. Their common molecular target is cytoplasmic tubulin needed for the construction of the mitotic spindle. Their effects are especially evident on dividing cells. However, any other cell activity based on microtubular activity will also be blocked Growth factor inhibitors: growth factors are polypeptides or proteins which stimulate cell multiplication of tissues. These growth factors are recognised by specific membrane receptors. Most often these are tyrosine kinase receptors. A distinction is made between receptors having a single amino acid chain with the family of EGF (epithelial growth factor) receptors for example, and receptors having two amino acid chains e.g. receptors of vascular endothelial growth factor (VEGF) and platelet derived growth factor (PDGF) both highly involved in angiogenesis. By angiogenesis is meant all the processes which lead to the formation of new blood capillaries from the pre-existing vascular network. The inhibitors of angiogenesis are also called anti-angiogenic drugs. For the specific inhibition of these growth factors there are two classes of drugs:

Monoclonal antibodies: these are large molecules active via injection. They block either the extracellular region of the receptor and cause its internalisation within the cell, or attach themselves on the endogenous ligand and prevent recognition thereof by the receptor. Mention can be made for example of alemtuzumab, bevacizumab, cetuximab, ibritumomab, panitumumab, pertuzumab, rituximab, trastuzumab.

The inhibitors of tyrosine kinase: these are small molecules generally active via oral route and which act on the intracellular region of the receptor. They remain active when a ligand is attached to the receptor. For example mention can be made of dasatinib, erlotinib, gefitinib, imatinib, nicotinib, sunitinib, sorafenib.

Hormone therapy: the growth of tumours in some cancers such as breast, endometrium, prostate, thyroid cancers, are dependent on the presence of hormones e.g. 5-hydroxytestosterone, progesterone, oestrogens. Hormone therapy therefore uses inhibitors of the production of these hormones or of the action thereof. This class includes anti-aromatases and as examples mention can be made of anastrozole, letrozole, exemestane, formestane selective modulators of the oestrogen receptor such as tamoxifen, toremifene; negative regulators of the oestrogen receptor such as fulvestrant; anti-androgens e.g. bicalutamide, flutamide, nilutamide; LHRH agonists e.g. buserelin, goserelin, leuprorelin, nafarelin, triptorelin.

Immune response modifiers: the objective of these substances is to stimulate the anticancer immune response. These products essentially comprise interleukin 2 which is a cytokine having a major role in the regulation of the immune system, it is produced by genetic engineering; recombinant interleukin 2 has shown its efficacy in immunotherapy, and interferon α which is a glycoprotein produced by cells parasitized by a virus.

The mechanisms of action of anticancer drugs are not always known with precision however and are sometimes multiple. For example, some of the above-cited drugs can be classified in several categories.

By << cardiotoxicity >> is meant toxicity affecting the heart and/or the vessels. Therefore << cardiotoxic effects >> mean toxic effects affecting the heart and/or vessels.

Cardiotoxicity induced by chemotherapy and/or ionising radiation may assume several clinical appearances which differ greatly in their signs and consequences. Four clinical forms have been described as a function of their time of onset in relation to the start of anticancer treatment:

acute cardiotoxicity: the immediate signs of cardiotoxicity related to anticancer treatments are mainly represented by sinoatrial tachycardia or electrocardiogram abnormalities, such as altered repolarisation on the ST segment and T wave. These manifestations are very frequent and dose-independent. They may appear during treatment, but more frequently occur in the hours after the administration of treatment. This form of toxicity is rarely serious from a clinical viewpoint, and does not usually allow the predicted onset of chronic toxicity and is generally not a reason for withdrawal of treatment.

sub-acute cardiotoxicity: this form of toxicity may be seen a few days or few weeks after the last administration of anticancer treatment. Some of these complications such as ventricular rhythm disorders (e.g. ventricular fibrillation), pericarditis and/or myocarditis may be particularly severe and be life-threatening. The improvement of these signs without sequelae is possible however.

chronic cardiotoxicity: this form of chronic toxicity most often becomes clinically apparent several weeks or several months after the last course of chemotherapy. According to studies it is observed in 0.4 to 23% of patients treated for cancer and translates as congestive heart failure, predominantly left-side, with high mortality rate. Heart failure is clinically defined as << the state in which the heart is no longer able sufficiently to perfuse the peripheral organs at rest and on exercising >>. It may or may not be evidenced via the ventricular ejection fraction or the left ventricular ejection fraction defined as the ratio between the volume of systolic ejection and diastolic volume.

delayed cardiotoxicity: the long-term follow-up of patients treated with chemotherapy has shown, in particular in children, that one form of cardiac toxicity could be diagnosed several years even decades after the last administration of anticancer agent(s), even in patients who received lower accumulated doses than those conventionally reported to be toxic. In children the clinical expression of cardiotoxicity is less obvious than in an adult, most probably due to large contractile reserves. On this account young patients may remain asymptomatic for years before showing signs of heart failure. In these heart failure patients, 20% undergo a heart transplant and more than 40% display much delayed decompensation translating as electric and ultrasound anomalies of myocardial contractility. The particular mechanism of this cardiotoxicity is related to the fact that the number of cardiomyocytes is definitively established by the age of 6 months, heart growth subsequently occurring solely by fibre hypertrophy.

Although cardiovascular effects vary in relation to the anticancer treatments used, they often coexist most probably due to common mechanisms. Schematically they can be classified into different categories of symptoms (Hong et al. 200, Clin. Cardiol. 33, 733-737).

1/ Systolic cardiac dysfunction: by << systolic cardiac dysfunction >> is meant an anomaly of systolic function leading to insufficient blood ejection. Its onset is gradual on account of myocardial cell loss, a consequence of the direct cytotoxic effects of anticancer drugs such as anthracyclines, anthraquinones, monoclonal antibodies, tyrosine kinase inhibitors, alkylating agents, interferon α.

2/ Cardiac ischemia: by << cardiac ischemia >> is meant insufficient blood supply to the heart. Cardiac ischemia has been described in patients receiving antimetabolites, intercalating agents or antitumour antibiotics. In patients with a previous history of heart disease, cardiac events can even go as far as myocardial infarction. Severe ischaemic attacks have also been described during the use of mitotic spindle poisons, growth factor inhibitors. It is possible that all antimitotic agents may damage vascular endothelium leading to cardiac ischemia.

3/ Cardiac arrhythmia: by << cardiac arrhythmia >> is meant a disturbed rhythm with irregular heartbeats. This rhythm disorders may result from direct cardiotoxicity but may also have an indirect cause. For example the administration of cisplatin or interleukin 2 increases capillary permeability and induces a reduction in intravascular volume possibly leading to ventricular arrhythmia. Numerous anticancer agents lengthen the QT interval and the association of such drugs may have dramatic effects.

4/ Pericarditis: by pericarditis is meant inflammation of the pericardium. They have been described in patients undergoing treatment with alkylating or antimetabolite agents.

5/ Thrombo-embolic complications: these are chiefly associated with the use of growth factor inhibitors, modulators of the oestrogen and progesterone receptors.

6/ The use of ionising radiation during chest radiotherapy increases the risk of constrictive pericarditis, myocardial fibrosis but also of valve and coronary artery lesions.

In addition, cardiovascular problems are aggravated when several anticancer drugs are used in combination and/or are associated with chest radiotherapy. Also, young cancer patients or on the contrary elderly cancer patients or those accumulating cardiovascular risk factors are particularly sensitive. For example anthracyclines or 5-fluoro-uracil are contra-indicated in cancer patients having a previous cardiovascular history. By << young cancer patients >> it is meant patients under the age of 30 and preferably under the age of 20. By << elderly cancer patients >> is meant patients older than 60 and preferably older than 70. By << suffering from cardiovascular disease >> is meant any disease which affects the cardiovascular system, mention being made for example of arterial hypertension, angina pectoris, heart failure, rhythm disorders, venous and/or arterial diseases, diabetes. By << accumulating cardiovascular risk factors >> is meant patients having at least 2 cardiovascular risk factors among all existing cardiovascular risk factors and for example arterial hypertension, obesity, diabetes, high cholesterol level, physical inactivity.

Some adjuvant drugs such as COX inhibitors, very frequently used to combat the pain associated with cancer, themselves have harmful effects on the cardiovascular system in addition to those of the anticancer treatments (Senkus and Janssem 2011, Cancer Treatment Reviews, 37, 300-311).

Finally, cardiotoxicity generally being accumulative, lengthy anticancer treatment even at low dose may become cardiotoxic over the long term.

Globally, anticancer drugs irrespective of their mechanism of action cause cardiovascular complications that are evidently undesirable. The quality of life of a significant proportion of patients both of those undergoing treatment and those on extended remission or cured of their cancer, is much diminished as a result. The extent of the problem is such that it is the subject of a new medical specialisation: onco-cardiology (Eschenhagen et al. 2011, Eur. J. Heart Fail. 13, 1-10). In this respect, it is distinctly more advantageous from every point of view to prevent the onset of cardiovascular problems/diseases caused by anticancer treatments than to endeavour to treat these after their onset.

The prevention of cardiotoxic effects entails the prevention of the onset thereof in a patient who does not suffer from any sign/symptom of cardiovascular type (primary prevention) but also entails preventing the aggravation thereof in patients in whom they are already present (secondary prevention).

By treatment of cardiotoxic effects is meant the disappearance or improvement of the said effects.

Various strategies are used to reduce the incidence and/or seriousness of the side effects of anticancer drugs, and hence of cardiovascular effects which are included therein. For example, it is possible to increase the concentration of the active ingredient(s) at the tumour and/or target organ using physical, physicochemical, dose form means or selective addressing. Another approach, more specifically focused on protection of the cardiovascular system, uses dexrazoxane, the only drug approved for cardiotoxicities induced by doxorubicin. However its use is increasingly a subject of dispute. Other drugs such as erythropoietin, thrombopoietin and iloprost have proved to be potentially useful in the prevention of cardiotoxicity due to anthracyclines in animal models but have not been assessed in human clinical studies (Li et al. 2006, Circulation 113, 535-543; Li et al. 2006, Circulation 113, 2211-2220).

According to this latter approach, the protective agent must clearly act solely at the cells of the cardiovascular system and must not under any circumstances oppose the anti-tumour action of the treatment. The selective action of the protective agent is therefore an essential criterion which is not met with existing agents such as dexrazoxane and other iron chelating agents and/or antioxidants whose mechanisms of action tend to interfere with that of anticancer treatments and thereby harm the cancer-treating efficacy thereof.

There is therefore a need in the state of the art for the identification of substances capable of selectively protecting the cardiovascular system against the toxic effects of anticancer drugs and/or ionising radiation.

Unexpectedly, the inventors have discovered that 3-(R)-[3-(2-methoxyphenylthio)-2-(S)-methyl-propyl]amino-3,4-dihydro-2H-1,5-benzoxathiepine or one of the pharmaceutically acceptable salts thereof is capable of selectively protecting the cardiovascular system against the toxic effects of anticancer drugs and/or ionising radiation. In this respect, 3-(R)-[3-(2-methoxyphenylthio)-2-(S)-methyl-propyl] amino-3,4-dihydro-2H-1,5-benzoxathiepine therefore meets a major medical need.

In the present invention << pharmaceutically acceptable >> refers to molecular entities and compositions which do not produce any adverse, allergic effects or other undesirable action when administered to a human. When used herein << pharmaceutically acceptable excipient >> includes any diluent, adjuvant or excipient such as preserving agents, filler agents, disintegrating, wetting, emulsifying, dispersing, antibacterial or antifungal agents, or agents which allow delayed absorption and delayed intestinal and digestive resorption. The use of these media or vectors is well known to persons skilled in the art.

By << pharmaceutically acceptable salts >> of a compound it is meant the salts defined herein and which have the pharmacological activity of the parent compound. Said salts comprise: acid addition salts formed with mineral acids such as hydrochloric acid, hydrobromic acid, sulphuric acid, nitric acid, phosphoric acid and similar, or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and similar.

The pharmaceutically acceptable salts also comprise the addition forms of solvents (solvates) or the crystalline forms (polymorphous) such as defined herein, of the same acid addition salt.

3-(R)-[3-(2-methoxyphenylthio)-2-(S)-methyl-propyl]amino-3,4-dihydro-2H-1,5-benzoxathiepine is a selective blocker of the slow sodium current produced by the Nav1.5 voltage-dependent channel abbreviated herein to slow Nav1.5 sodium current. It is important to note that this compound is not cytotoxic and does not have antioxidant properties.

Blocking of the slow Nav1.5 sodium current does not belong to the mechanisms used by anticancer drugs and ionising radiation to destroy and/or limit tumour growth.

The Nav1.5 channel is essentially distributed at the muscle cells of the heart and blood vessels. In addition, the slow Nav1.5 sodium current does not play any role in the normal functioning of the heart and vascular cells. In this respect, the inventors have already shown that 3-(R)-[3-(2-methoxyphenylthio)-2-(S)-methyl-propyl]amino-3,4-dihydro-2H-1,5-benzoxathiepine, even in strong concentrations, does not affect the normal functioning of the cardiovascular system.

Having regard to its particular mode of action the inventors have surprisingly shown that 3-(R)-[3-(2-methoxyphenylthio)-2-(S)-methyl-propyl]amino-3,4-dihydro-2H-1,5-benzoxathiepine, or one of its pharmaceutically acceptable salts, prevents or strongly attenuates cardiotoxicity induced by doxorubicin without however reducing its toxicity for cancer cells.

On the basis of this observation, the inventors consider that the slow Nav1.5 sodium current is produced or amplified when the heart and/or vascular cells are subjected to the action of doxorubicin or more generally of one or more anticancer drugs and/or ionising radiation.

The inventors also consider than the slow Nav1.5 sodium current produced or amplified in the cardiomyocytes in response to exposure to anticancer drugs and/or ionising radiation is responsible for their cardiotoxicity.

Therefore the selective blocking of the slow Nav1.5 sodium current can allow the preventing of the cardiotoxicity of anticancer drugs and/or ionising radiation without reducing the cancer-treating efficacy thereof.

Consequently, 3-(R)-[3-(2-methoxyphenylthio)-2-(S)-methyl-propyl]amino-3,4-dihydro-2H-1,5-benzoxathiepine and its pharmaceutically acceptable salts have the required and essential selectivity of action for use as protective agent of the cardiovascular system, in particular during anticancer treatments.

The present invention concerns the use of 3-(R)-[3-(2-methoxyphenylthio)-2-(S)-methyl-propyl]amino-3,4-dihydro-2H-1,5-benzoxathiepine, or one of its pharmaceutically acceptable salts, as drug for the prevention and/or treatment of the cardiotoxic effects due to anticancer drugs and/or ionising radiation.

The present invention concerns the use of 3-(R)-[3-(2-methoxyphenylthio)-2-(S)-methyl-propyl]amino-3,4-dihydro-2H-1,5-benzoxathiepine or one of its pharmaceutically acceptable salts as drug for the prevention and/or treatment of the cardiotoxic effects due to anticancer drugs chosen from alkylating agents, antimetabolites, DNA modifiers, anti-tumour antibiotics, mitotic spindle poison derivatives, growth factor inhibitors, modifiers of immune and hormonal response and/or possible associations of these different categories of drugs.

The present invention also concerns the use of 3-(R)-[3-(2-methoxyphenylthio)-2-(S)-methyl-propyl]amino-3,4-dihydro-2H-1,5-benzoxathiepine or one of its pharmaceutically acceptable salts as drug for the prevention and/or treatment of the cardiotoxic effects due to ionising radiation and/or to the association of ionising radiation with the different classes of anticancer drugs According to the present invention the cardiotoxic effects due to anticancer drugs and/or to ionising radiation preferably translate either as rhythm disorders, cardiac ischemia, systolic cardiac dysfunction, pericarditis, thrombophilia, or even heart failure.

The present invention concerns treated cancer patients whose ventricular ejection fraction or left ventricular ejection fraction is lower than normal on the initiation of anticancer treatment, or those having a ventricular ejection fraction which decreases throughout the course of this treatment.

The present invention also concerns treated cancer patients who are either young or elderly, suffering from a cardiovascular disease or who accumulate cardiovascular risk factors.

3-(R)-[3-(2-methoxyphenylthio)-2-(S)-methyl-propyl]amino-3,4-dihydro-2H-1,5-benzoxathiepine or one of its pharmaceutically acceptable salts can be administered simultaneously with anticancer treatments or separately or sequentially. It can also be used throughout the entire duration or over a shorter or longer period than the period of anticancer treatment.

A further subject of the invention concerns the use of 3-(R)-[3-(2-methoxyphenylthio)-2-(S)-methyl-propyl]amino-3,4-dihydro-2H-1,5-benzoxathiepine or one of its pharmaceutically acceptable salts for the preparation of a drug intended for the prevention or treatment of cardiotoxicity occurring during or after one or more anticancer treatments The present invention further concerns a pharmaceutical composition containing 3-(R)-[3-(2-methoxyphenylthio)-2-(S)-methyl-propyl]amino-3,4-dihydro-2H-1,5-benzoxathiepine or one of its pharmaceutically acceptable salts as active ingredient and at least one pharmaceutically acceptable excipient.

The pharmaceutical compositions of the present invention can be formulated for administration to the human being. The compositions of the invention can be administered via oral, sublingual, subcutaneous, intramuscular, intravenous, transdermal, local or rectal routes, or via intra-nasal route. In this case the active ingredient can be administered in unit administration forms in a mixture with conventional pharmaceutical carriers, to human beings. Suitable unit administration forms comprise forms for oral route such as tablets, capsules, powders, granules and oral solutions or suspensions, sublingual and buccal administration forms, subcutaneous or transdermal administration forms, topical, intramuscular, intravenous, intra-basal or intraocular forms, rectal administration forms.

When preparing a solid composition in the form of tablets, the main active ingredient is mixed with a pharmaceutical carrier such as gelatine, starch, lactose, magnesium stearate, talc, gum arabic, silica or similar. The tablets can be coated with sucrose or other suitable materials or they can be treated so that they have sustained or delayed action, and continuously releasing a predetermined quantity of active ingredient.

A capsule preparation is obtained by mixing the active ingredient with a diluent and pouring the mixture obtained into soft or hard capsules.

A preparation in syrup or elixir form can contain the active ingredient together with a sweetener, an antiseptic, and a suitable flavour enhancer and colouring agent.

The powders or granules dispersible in water can contain the active ingredient in a mixture with dispersing agents or wetting agents, or suspending agents, also with flavour enhancers or sweeteners.

For rectal administration, suppositories prepared with binders melting at rectal temperature e.g. cocoa butter or polyethylene glycols are used.

For parenteral (intravenous, intramuscular, intradermal, subcutaneous), intra-nasal or intraocular administration, use is made of aqueous suspensions, isotonic saline solutions or sterile injectable solutions containing pharmacologically compatible dispersing agents and/or wetting agents.

The active ingredient may also be formulated in the form of microcapsules optionally with one or more added carriers.

Advantageously the pharmaceutical composition of the present invention is intended for administration via oral or intravenous route.

The pharmaceutical composition of the present invention can be administered simultaneously with the anticancer drugs or separately or sequentially. It can also be used throughout the entire duration or over a shorter or longer period than the period of the anticancer treatment.

The pharmaceutical composition of the present invention may comprise other active ingredients leading to a complementary or optionally synergic effect.

The doses of 3-(R)-[3-2-methoxyphenylthio)-2-(S)-methyl-propyl]amino-3,4-dihydro-2H-1,5-benzoxathiepine or one of its pharmaceutically acceptable salts in the compositions of the invention can be adjusted to obtain a quantity of substance that is efficient to obtain the desired therapeutic response with a composition particular to a given administration method. The efficient dose of the compound of the invention varies in relation to numerous parameters such as the chosen route of administration, the patient's weight, age, gender, type of pathology, type of anticancer treatment(s) administered and the sensitivity of the individual to be treated. Therefore the optimal dosage must be determined by the specialist in the matter in relation to the parameters considered relevant. Although the efficient doses may vary within large proportions, the daily doses could range from 1 mg to 1000 mg per 24 hours, and preferably between 1 and 200 mg, for an adult of 70 kg average weight, taken in one or more times.

The invention will be better understood with reference to the following example and FIGURE.

It has been shown by the invention that 3-(R)-[3-(2-methoxyphenylthio)-2-(S)-methyl-propyl]amino-3,4-dihydro-2H-1,5-benzoxathiepine has the remarkable and unexpected property of preserving the viability of cardiomyocytes exposed to toxic concentrations of an anticancer drug: doxorubicin. In the present invention, doxorubicin was chosen solely for illustrative purposes on the basis of its recognised cardiotoxicity. Evidently the usefulness of 3-(R)-[3-(2-methoxyphenylthio)-2-(S)-methyl-propyl]amino-3,4-dihydro-2H-1,5-benzoxathiepine or one of its pharmaceutically acceptable salts extends to the other anticancer drugs or combinations thereof and to ionising radiation.

The effects of 3-(R)-[3-(2-methoxyphenylthio)-2-(S)-methyl-propyl]amino-3,4-dihydro-2H-1,5-benzoxathiepine were assessed in the following cell model: rat cardiomyocytes were placed in culture either in the presence or in the absence of doxorubicin. After 48 hours, cell suffering was quantified by assay of the concentration of lactate dehydrogenase (LDH); LDH is a marker of anaerobic glycolysis.

It was found that doxorubicin at a concentration of 1 and 10 μM significantly affects the viability of cardiomyocytes in a significant manner and comparable with that of a toxic agent chosen as reference: Triton X-100 (see appended FIGURE). It was also found that 3-(R)-[3-(2-methoxyphenylthio)-2-(S)-methyl-propyl]amino-3,4-dihydro-2H-1,5-benzoxathiepine at a concentration of 10 μM significantly reduces the toxic effects of doxorubicin and thereby preserves the viability of cardiomyocytes.

Doxorubicin is not known to interact directly with the Nav1.5 sodium channel. According to the results of the experiment it is nevertheless clear that the said channel plays a determinant role in the cardiotoxicity of doxorubicin. On the basis of this surprising observation, and without detriment to the details of the mechanisms of the cytotoxicity involved by doxorubicin and more generally by anticancer treatments, the inventors suggest that the slow Nav1.5 sodium current produced by a cardiomyocyte in response to its exposure to doxorubicin is necessary and sufficient to account for its toxicity and more generally that of anticancer treatments. In other words, in the cardiac and vascular cells the expression or amplification of the slow sodium current produced by the Nav1.5 channel represents a common response to anticancer treatments and is responsible for the onset of cardiotoxicities.

It is important to note that in cancer cell lines sensitive to doxorubicin, the mixture of doxorubicin/3-(R)-[3-(2-methoxyphenylthio)-2-(S)-methyl-propyl]amino-3,4-dihydro-2H-1,5-benzoxathiepine is at least as cytotoxic for tumour cells as doxorubicin alone. 3-(R)-[3-(2-methoxyphenylthio)-2-(S)-methyl-propyl]amino-3,4-dihydro-2H-1,5-benzoxathiepine does not therefore interfere with the mechanisms responsible for the cytotoxicity of doxorubicin for cancer cells.

The invention claimed is:

1. A method for preventing the cardiotoxic effects due to doxorubicin by administration to a patient in need thereof of an effective amount of 3-(R)-[3-(2-methoxyphenylthio)-2-(S)-methyl-propyl]amino-3,4-dihydro-2H-1,5-benzoxathiepine or one of its pharmaceutically acceptable salts.

2. The method according to claim 1, wherein the cardiotoxic effects translate as rhythm disorders, cardiac ischemia, systolic cardiac dysfunction, pericarditis, thrombophilia, and/or heart failure.

3. The method according to claim 1, wherein the patient does not currently suffer from cardiovascular disease.

4. The method according to claim 1, wherein the patients are treated cancer patients who are young or elderly and/or suffering from cardiovascular disease and/or accumulating cardiovascular risk factors.

5. The method according to claim 1, wherein the patients are treated cancer patients having a ventricular ejection fraction or left ventricular ejection fraction lower than normal on initiation of anticancer treatment, or those having a ventricular ejection fraction which decreases throughout the course of this treatment.

6. A method for preventing the cardiotoxic effects due to doxorubicin by administration to a patient in need thereof of an effective amount of a pharmaceutical composition containing, as active ingredient, 3-(R)-[3-(2-methoxyphenylthio)-2-(S)-methyl-propyl]amino-3,4-dihydro-2H-1,5-benzoxathiepine or one of its pharmaceutically acceptable salts and at least one pharmaceutically acceptable excipient.

7. The method according to claim 6, wherein the cardiotoxic effects translate as rhythm disorders, cardiac ischemia, systolic cardiac dysfunction, pericarditis, thrombophilia, and/or heart failure.

8. The method according to claim 6, wherein the patient does not currently suffer from cardiovascular disease.

9. The method according to claim 6, wherein the patients are treated cancer patients having a ventricular ejection fraction or left ventricular ejection fraction lower than normal on initiation of the anticancer treatment, or those having a ventricular ejection fraction which decreases throughout the course of this treatment.

10. The method according to claim 6, wherein the pharmaceutical composition is administered via oral or intravenous route.

11. The method according to claim 6, wherein the pharmaceutical composition is administered simultaneously with doxorubicin.

12. The method according to claim 6, wherein the pharmaceutical composition is administered separately or sequentially in relation to doxorubicin.

13. The method according to claim 6, wherein the pharmaceutical composition is in the form of a daily dosage unit of 3-(R)-[3-(2-methoxyphenylthio)-2-(S)-methyl-propyl]amino-3,4-dihydro-2H-1,5-benzoxathiepine or one of its pharmaceutically acceptable salts, of between 1 and 1000 mg.

14. A method for preventing pericarditis or thrombophilia due to doxorubicin by administration to a patient in need thereof of an effective amount of 3-(R)-[3-(2-methoxyphenylthio)-2-(S)-methyl-propyl]amino-3,4-dihydro-2H-1,5-benzoxathiepine or one of its pharmaceutically acceptable salts.

15. The method according to claim 14, wherein the patients are treated cancer patients who are young or elderly and/or suffering from cardiovascular disease and/or accumulating cardiovascular risk factors.

16. The method according to claim 14, wherein the patients are treated cancer patients having a ventricular ejection fraction or left ventricular ejection fraction lower than normal on initiation of anticancer treatment, or those having a ventricular ejection fraction which decreases throughout the course of this treatment.

17. A method for preventing pericarditis or thrombophilia due to doxorubicin by administration to a patient in need thereof of an effective amount of a pharmaceutical composition containing, as active ingredient, 3-(R)-[3-(2-methoxyphenylthio)-2-(S)-methyl-propyl]amino-3,4-dihydro-2H-1,5-benzoxathiepine or one of its pharmaceutically acceptable salts and at least one pharmaceutically acceptable excipient.

18. The method according to claim 17, wherein the patients are treated cancer patients having a ventricular ejection fraction or left ventricular ejection fraction lower than normal on initiation of the anticancer treatment, or those having a ventricular ejection fraction which decreases throughout the course of this treatment.

19. The method according to claim 17, wherein the pharmaceutical composition is administered via oral or intravenous route.

20. The method according to claim 17, wherein the pharmaceutical composition is administered simultaneously with doxorubicin.

21. The method according to claim 17, wherein the pharmaceutical composition is administered separately or sequentially in relation to doxorubicin.

22. The method according to claim 17, wherein the pharmaceutical composition is in the form of a daily dosage unit of 3-(R)-[3-(2-methoxyphenylthio)-2-(S)-methyl-propyl]amino-3,4-dihydro-2H-1,5-benzoxathiepine or one of its pharmaceutically acceptable salts, of between 1 and 1000 mg.

* * * * *